(12) United States Patent
Chan et al.

(10) Patent No.: US 9,568,425 B2
(45) Date of Patent: Feb. 14, 2017

(54) MULTICODED ANALYTICAL NANOSTRIPS

(75) Inventors: Eugene Y. Chan, Boston, MA (US); Moon Z. Chan, Boston, MA (US)

(73) Assignee: DNA Medicine Institute, Inc., Cambridge, MA (US)

( * ) Notice: Subject to any disclaimer, the term of this patent is extended or adjusted under 35 U.S.C. 154(b) by 36 days.

(21) Appl. No.: 13/361,914

(22) Filed: Jan. 30, 2012

(65) Prior Publication Data

US 2012/0196382 A1 Aug. 2, 2012

Related U.S. Application Data

(60) Provisional application No. 61/462,336, filed on Feb. 1, 2011.

(51) Int. Cl.
*B82Y 15/00* (2011.01)
*G01N 21/64* (2006.01)
(Continued)

(52) U.S. Cl.
CPC ..... *G01N 21/6428* (2013.01); *B01L 3/502761* (2013.01); *B82Y 15/00* (2013.01);
(Continued)

(58) Field of Classification Search
CPC ............... B01L 2300/0816; B01L 2300/0825; B01L 2300/02; B01L 2200/025; B01L 2400/0406; B01L 3/5027; G01N 33/53; G01N 33/543; G01N 33/54373; G01N 33/54386; G01N 33/54366; G01N 33/558; G01N 33/561; G01N 33/52; G01N 33/521; G01N 33/491; G01N 2035/00108; C12Q 2563/149; C12Q 2537/143; C12Q 2545/101; C12Q 2563/155; B01J 2219/005; B01J 2219/00545; B01J 2219/00549; B01J 2219/00576; B01J 2219/00596; B01J 2219/00722; B01J 2219/00725
(Continued)

(56) References Cited

U.S. PATENT DOCUMENTS 7,595,160 B2 9/2009 White et al.
7,709,544 B2 5/2010 Doyle et al.
(Continued)

FOREIGN PATENT DOCUMENTS

WO WO 2007075894 A2 * 7/2007
WO WO 2008063758 A2 * 5/2008

OTHER PUBLICATIONS

Pregibon et al., Multifunctional Encoded Particles for High-Throughput Biomolecule Analysis, 2007, Science, vol. 315, pp. 1393-1396.*
(Continued)

*Primary Examiner* — Erik B Crawford
(74) *Attorney, Agent, or Firm* — Robert S. Blasi, Esq.; Danielson Legal LLC

(57) ABSTRACT

Analytical nanostrips for clinical analysis are improved by using multifunctional coding ("multicoding") to allow simultaneous identification of the particular assay, the value of the assayed analyte, and a calibration of the analyte. The multicoding layout on the nanostrip minimizes the number of zones that are required for a given assay. Moreover, the nanostrip can be scanned in real time during flow of the nanostrip through a detection beam. This both simplifies the assay and allows for alternative means of coding.

17 Claims, 5 Drawing Sheets

(51) Int. Cl.
   *G01N 33/58*   (2006.01)
   *G01N 33/543*  (2006.01)
   *B01L 3/00*    (2006.01)
   *G01N 21/21*   (2006.01)

(52) U.S. Cl.
   CPC ....... *G01N 21/21* (2013.01); *G01N 33/54313* (2013.01); *G01N 33/582* (2013.01); *G01N 33/587* (2013.01); *B01L 2200/0647* (2013.01); *B01L 2200/0663* (2013.01); *G01N 33/54346* (2013.01); *G01N 2021/6441* (2013.01)

(58) Field of Classification Search
   USPC ....... 977/788–808, 836, 897, 902, 904, 918, 977/920, 924
   See application file for complete search history.

(56) References Cited

U.S. PATENT DOCUMENTS

| | | | |
|---|---|---|---|
| 7,749,445 B2 | 7/2010 | Masters | |
| 7,947,487 B2* | 5/2011 | Doyle et al. | 435/283.1 |
| 2004/0214347 A1* | 10/2004 | LaBorde et al. | 436/518 |
| 2007/0105972 A1* | 5/2007 | Doyle | B81C 99/0095 522/1 |
| 2008/0176216 A1* | 7/2008 | Doyle et al. | 435/5 |
| 2009/0215032 A1* | 8/2009 | White et al. | 435/6 |
| 2010/0330693 A1* | 12/2010 | Chapin et al. | 436/172 |
| 2011/0136104 A1* | 6/2011 | Pregibon et al. | 435/6 |
| 2012/0107820 A1* | 5/2012 | Pregibon et al. | 435/6.11 |
| 2012/0214224 A1 | 8/2012 | Chan | |
| 2012/0309651 A1* | 12/2012 | Pregibon | C12Q 1/6816 506/16 |
| 2012/0316082 A1* | 12/2012 | Pregibon et al. | 506/9 |
| 2013/0210653 A1* | 8/2013 | Pregibon et al. | 506/9 |

OTHER PUBLICATIONS

Pearce et al., Multifunctional Nanorods for Biomedical Applications, 2007, Pharmaceutical Research, vol. 24, No. 12, pp. 2335-2352.*

* cited by examiner

Figure 5

| | | | | | | | | | |
|---|---|---|---|---|---|---|---|---|---|
| A | C1 | C2 | C3 | C4 | C5 | S1 | S2 | S3 | S4 |
| B | C1 | C2 | S1 | C3 | S2 | S3 | C4 | C5 | S4 |
|   | X | - | X | X | - | - | X | - | - |
| C | C1 | S1 | C2 | S2 | C4 | C5 | S3 | C3 | S4 |
|   | X | X | - | - | X | X | - | - | - |

MULTICODED ANALYTICAL NANOSTRIPS

This application claims the benefit of the priority of provisional patent application 61/462,336 entitled "Multicoded Analytical Nanostrips", which was filed on Feb. 13, 2012 and which is incorporated herein by reference in its entirety.

BACKGROUND

A system is being developed for clinical analysis using components that are significantly smaller than current analysis systems, and suitable for use in remote environments, such as space flight. Current systems for assaying medically-relevant parameters of blood typically require taking one or more venous blood samples, which are then analyzed in one or more large, specialized clinical autoanalyzer systems. Such systems, besides being bulky, generate significant volumes of medical waste, which must be treated as a hazardous material.

Moreover, current systems are often highly automated, and have dedicated staff to manage the flow of samples through the machine. Such systems are well adapted to hospitals and clinics. However, there are numerous situations which require more flexibility in a clinical analyzer, and which in particular have a low volume of sampling, requiring an analyzer which is suitable for intermittent use. Often, such requirements are presented by isolated populations or locations.

Such a flexible analyzer system is preferably highly automated in operation, so that it can be used without extensive training. Moreover, it should avoid or minimize the amount of waste generated, by minimizing the need for large samples and by flexibly running multiple assays on a single small sample (e.g., a finger prick vs. a sample from a vein). At the same time, it should have the ability to be used only intermittently, rather than daily or continuously as in most current analyzers. The system should also be flexible, to allow a wide variety of assays to be analyzed.

One important part of a system for accomplishing these objectives is a simple device and method for sample dilution, mixture of a sample with reagents, and delivery of the diluted sample to a flow cell for quantification of one or more parameters. Another important aspect of the system is the ability to work with small samples of blood or other bodily fluid, with sample volumes in the sub-milliliter range, for example 3 to 100 microliters. A related aspect of the system is the ability to perform continuous fluid flow at low differential pressures, to prevent leakage of components and for safety. Another aspect of the system is to provide an automated readout that is self-calibrated and that identifies the assay.

One route to these objectives is by size reduction of assay materials and systems. Several groups have shown that clinical analysis and similar laboratory procedures can be performed on devices that are greatly reduced in size compared to current clinical assay procedures. For example, White and Gilmanshin, in U.S. Pat. No. 7,595,160, use a nucleic-acid based probe of about 7.5-15 kilobases attached to antibodies, and so having an effective length of 10-20 microns for the DNA sequence. Doyle et al, in U.S. Pat. No. 7,709,544, describe a method of making small objects having different zones, by flowing parallel streams through a channel and polymerizing material contained in said streams. Masters, in U.S. Pat. No. 7,749,445, uses mixtures of sample materials with These groups have demonstrated that clinical assays can be miniaturized and fabricated as nanostrips, and that nanostrips can be read by an optical system, for example by laser excitation of chromophores attached to reagents. In many cases, assays are evaluated by analysis of images of microstrips. However, while the general feasibility of such a system has now been hypothesized for nearly a decade, there are still no actual systems of this sort on the market.

One of the limitations of prior microanalysis systems, using very small assay strips containing several zones, is the need to optically identify four different variables on each microchip passing through an analysis system. The first variable is the actual analytic result—for example, the amount of a particular protein or metabolite in a blood sample. These are the results actually delivered to the physician and the patient.

The second variable is a calibration procedure for the assay. It is highly desirable to have the assay nanostrip be self-calibrated, so that the reading of the analytic result is calibrated in real time-preferably on the same nanostrip, or in a reference nanostrip incubated in the same solution. This removes a variety of types of error that otherwise could occur.

The third variable is the identification of the assay. The nanostrips are platforms for assay, and are usable for many different assays. The system used to read the analytic result must also be able to issue a reliable output for identifying the assay being performed.

The fourth variable is the directionality of the nanostrip being analyzed. In the system of the invention, the nanostrip being read can enter the reading zone with either end leading.

In practice, an efficient implementation of the integration of these functions is required, so that the nanostrips of the invention are reliable and readily useable. Moreover, the system is preferably small enough and light enough to be portable, and simple enough to be used without lengthy training.

SUMMARY OF THE INVENTION

In a first aspect, the nanostrip of the invention comprises an elongated strip comprising a plurality of assay zones. Each of the zones is capable of being measured to determine its position along the strip, as well as to determine the value of one or more readings of the properties of each zone. The analytical instrument can then determine, from the analysis of the measured properties of a plurality of zones on one or more strips, data suitable for use in the determination of all relevant properties of the analysis, including at least a measurement of the concentration of an analyte, a measurement of the concentration of at least one standard, a detectable signature identifying the assay, and a detectable signal, if required, for determining the directionality of the strip being analyzed.

The nanostrips of the invention are used in a flow assay system. Such a system operates by mixing nanostrips in a solution, such as buffered saline, with a sample to be analyzed. The mixture interacts during a flow interval, which is the interval between the time of the mixing, and the time of passing of the mixture through a measurement apparatus. During this interval, which in the present invention is typically in the range of seconds, and preferably less than a minute, the material to be assayed interacts with materials on the nanostrip sufficiently to provide a useful, stable reference signal.

The measurements derived from the nanostrip are generally remote, non-contact measurements suitable for evaluating samples on nanostrips that pass through a detection region in a flowing stream. Optical measurements, such as absorbance, fluorescent emission, polarization, and light scattering, at one or more wavelengths, are preferred. Other types of measurement can also be used in the system, including but not limited to electrical or acoustic impedance, or other physical-property measurements suitable for detection in a flowing stream containing nanostrips.

The measurement system includes at least one detection station in the system. A second detection station can also be used if it is nearby on the detector flow path, so that chip identity can be assumed between the spatially separate readings.

In a preferred embodiment, the presence of a set of standards of defined values is determined by the value of a standardizing signature, which is the measurement of an optical or other property of several of the zones of the strip, correlated with their position along the strip. Examples of measurements include the absorption or the emission of light at a selected wavelength, wherein the absorption or emission is proportional to the concentration of the standard. A standardizing signature will typically comprise readings of a standard or control at several concentrations, to allow generation of a standard curve against which the value of a measuring signature can be evaluated.

In particular, the signature of a standard is preferably measured by providing zones comprising a null standard concentration and at least a first standard concentration. In a more preferred embodiment of the invention, the concentration of the sample is determined by measurement of several different standardized levels of concentration of the standard, and fitting the results to a curve. The different levels need not be in contiguous zones or be arranged in order of monotonically changing values.

In a preferred embodiment, the concentration of an analyte is determined by the value of a measuring signature, which is the result of measuring a property of a sample in a zone of the nanostrip. This could be, for example, the absorption or the fluorescent emission of light at a selected wavelength, optionally and preferably in the same format and detection system as a standardizing signature for detection of a standard. The absorption or emission or other measured property in the measuring signature is proportional to the concentration of the analyte, and is converted to a measured value by comparison with the standardizing signature.

In a preferred embodiment, at least some zones on the analytical nanostrip of the invention serve more than one function. In a preferred embodiment, the sequence of standardized concentrations of the invention is used analytically to determine the directionality of the chip being analyzed.

In a preferred embodiment, the assay identification detection function ("bar code") is provided by the presence (or absence) in several zones of a detectable bar code signature. The bar code signature can be binary (present or absent) or quantitative (giving a value). The bar code may also serve as a means of determination of directionality. The bar code may be analyzed by a different wavelength or by a different detection method than the measurements of the standardizing and measuring signatures.

In a preferred embodiment, an analytical nanostrip for performing an assay on a sample is provided, said nanostrip comprising multiple zones, said zones including at least measurement zones and identification zones, and said identification zones including at least zones for identifying the assay, wherein the assay is characterized in that a plurality of zones have more than one function.

In a preferred embodiment, a majority of zones have more than one function, and the assay is analyzed on said nanostrip by one or more optical means, where said optical means may include one or more of absorption of light, emission of fluorescence, alteration of light polarization, and light scattering. In the analysis, one or two wavelengths of light may used for performing said assay, and one or two detectors. In addition, an assay may be analyzed in whole or in part by by a non-optical system.

In the plurality of zone functions, one of said zone functions is to be a part of an identification of assay type, and one of said functions is to be a part of an identification of nanostrip orientation. Another one of said functions is a measurement of a clinically-relevant parameter, and another one of said functions is to be a part of a calibration curve. The calibration curve zone values, or their arrangement on the strip, may part of an identification of assay type, or may be part of an identification of strip reading direction.

The sample to be analyzed is detectable by incubation of said nanostrip with said sample under defined conditions. In particular, said assay creates a measureable change in a detectable property in at least one sample analysis zone of said nanostrip upon incubation with a sample for analysis. More information may be provided by having multiple zones detect said sample. In addition, two or more calibration curves may be present on said type of nanostrip, and two or more different analyses of a sample may be performed upon incubation of sample with a single type of nanostrip.

The invention also provides a method of analysis using a nanostrip, said nanostrip having a plurality of zones in a linear array, and each of said zones functioning as one or more of a sample analysis zone, a part of a calibration curve, and a part of an assay identification code; wherein when said nanostrip is incubated with a solution containing a sufficient amount of at least one analyte, at least one of the sample analysis zones of the nanostrip undergoes a detectable change in response to the presence of said analyte in said solution. The method further provides one or more of said zones having two functions, the functions selected from a sample analysis means, a part of a calibration curve, and a part of an assay identification code. Each of a plurality of calibration curve zones may also serve as a part of an assay identification zone. Said assay method creates a measureable change in a detectable property in at least one sample analysis zone, upon incubation with a sample for analysis.

In the method, two or more different analyses of a sample may be performed upon incubation of a sample with a single type of nanostrip. Zones for more than one calibration curve may be present on the same nanostrip. Said calibration curves may differ in the way that they are measured, and measurements may be made at two different optical wavelengths, and at least one measurement may non-optical. One wavelength may used for samples and calibration and another wavelength may be used for assay identification and orientation. A detectable change in said nanostrip may be a change in one or more of fluorescence, absorbance, light scattering, polarization, impedance, energy transfer, and chemilumnescence.

Said nanostrips may be read by flow of said nanostrips through a detector, and said nanostrips may be flow-oriented before or during passage through said detector. The zones of said nanostrip may be read sequentially during flow, and multiple zones may detect said sample.

BRIEF DESCRIPTION OF THE FIGURES

FIG. 5 shows an example of the ways a short nanostrip of the invention could be coded.

DETAILED DESCRIPTION OF THE INVENTION

Fabrication of the Nanostrips

The analytical nanostrips of the invention, and the system for analyzing them, have the ability to provide all four forms of information required for analysis (analytic result, calibration standard, assay identification, directionality) on a single nanostrip ("strip"). A single strip typically comprises a series of zones along the length of the strip. The zones of the strip are formed by a concurrent flow of reagents into a polymerization zone. Techniques of this sort are known, for example as illustrated in Doyle et al (U.S. Pat. No. 7,709,544).

Figure 1:
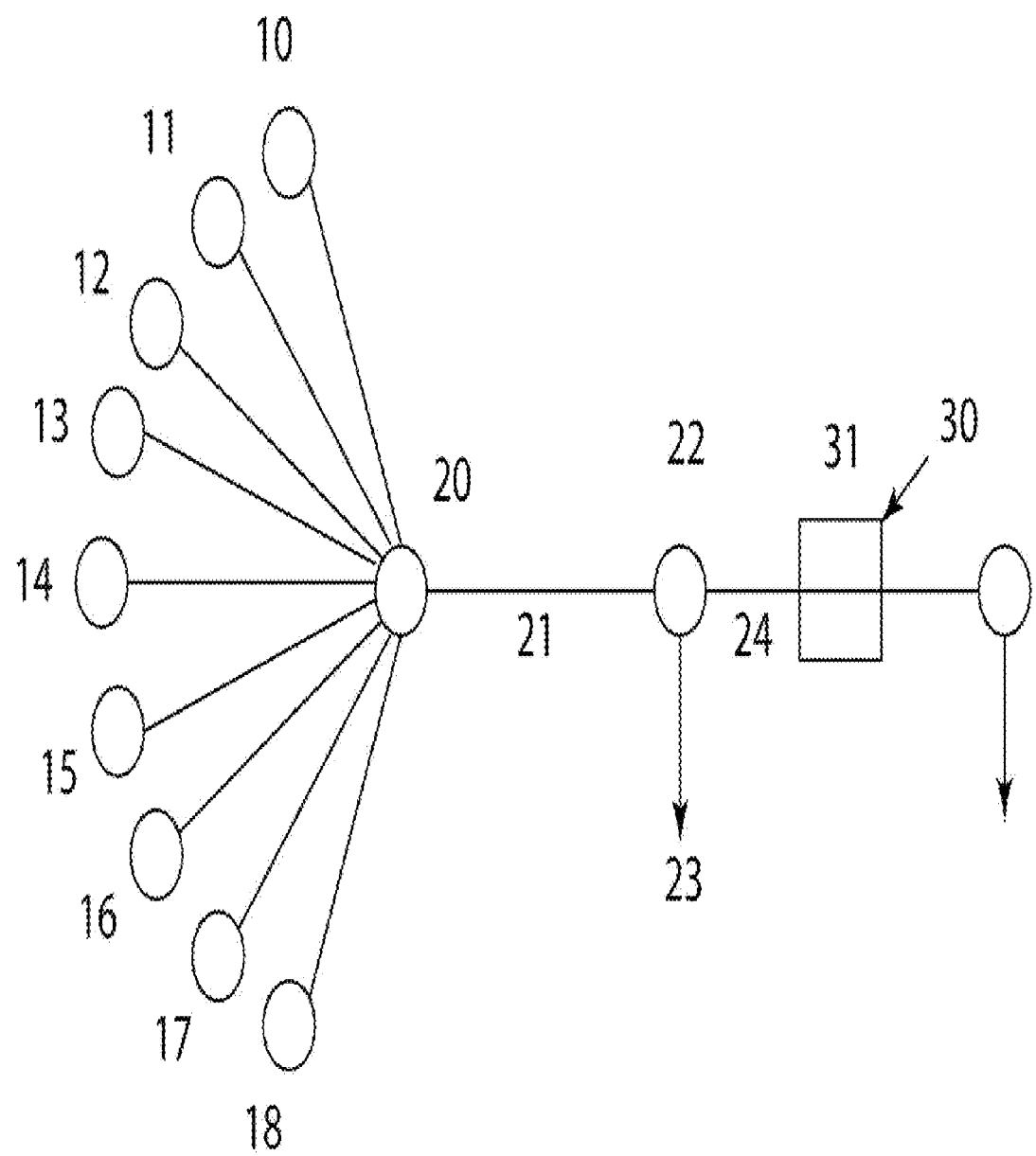
FIG. 1 shows a diagram of a system for preparation of a nanostrip, via convergence of flows and passage of the input flows to the polymerization zone.

FIG. 1 illustrates the nanostrip fabrication process of the present invention schematically. The nanostrips are made by polymerizing reactive monomers to form a hydrogel. The preferred method of polymerization is by absorption of light either by gel-forming components, or by photoactive catalysts for gel formation. Other forms of polymerization may also be used. Materials for nanostrip fabrication are typically short polymers having crosslinking ability, preferably photocrosslinkable. Preferred materials include polyethylene glycol diacrylate (PEG-DA, MW 200 to 3000). A currently preferred basic formulation is 60% PEG-DA (MW=700), 2% 2-hydroxy-2-methylpropiophenone photoinitiator, and 38% 1× PBS (phosphate buffered saline) or 1× Tris-EDTA buffer. The basic formulation is supplemented with detection and recognition analytes as required for the particular assay.

As shown schematically in FIG. 1, to manufacture a nanostrip of the invention, a plurality of reagents are fed through converging channels, in this case nine channels 10-18, to a formation region 20 in which the reagent streams converge and flow as laminae through channel 21 and thence through polymerization zone 30. Channel 21 is preferably an essentially rectangular channel, into which reagent flows from ports 10-18 are injected side-by-side. Each reagent stream contains a basic polymerization system, preferably photoactivatable, and one or more of an analytical reagent, a standard (which may be a null standard), and a marker. The streams are polymerized by passage through at least one beam of light 31 of an appropriate wavelength to stimulate polymerization.

In a preferred embodiment, the flow of the streams is briefly stopped during polymerization. After polymerization is completed, light is optionally blocked or turned off, and flow is resumed. After a sufficient lag time to create an unpolymerized fluid zone separating strips, the light is again applied to the sample. It is potentially useful to create the unpolymerized fluid zone by turning off or blocking the polymerizing light source, but it is not essential if the intensity of the polymerizing light and the duration of exposure are carefully standardized. The utility of actually blocking flow during polymerization is to produce relatively uniform polymerization in the region exposed to the light. Under some conditions, a combination of halting of flow during light exposure, and blocking of light while resuming and ceasing flow, may be advantageous. In the example of FIG. 1, a method of interrupting flow is to position a three-way valve 22 in the flow path before the flow enters a polymerization zone 31. Then, to polymerize a strip of gel, the flow is diverted briefly at valve 22 while a polymerizing stimulus, such as a light beam, is delivered to the polymerizable gel forming reagents that are in the path of the beam. After sufficient exposure to induce polymerization, valve 22 is changed so that flow through the polymerization path is resumed. Alternatives include interruption of a flow-inducing pressure, and direct blocking of the flow stream, before the streams enter the polymerization region, or after they exit it.

Figure 2:
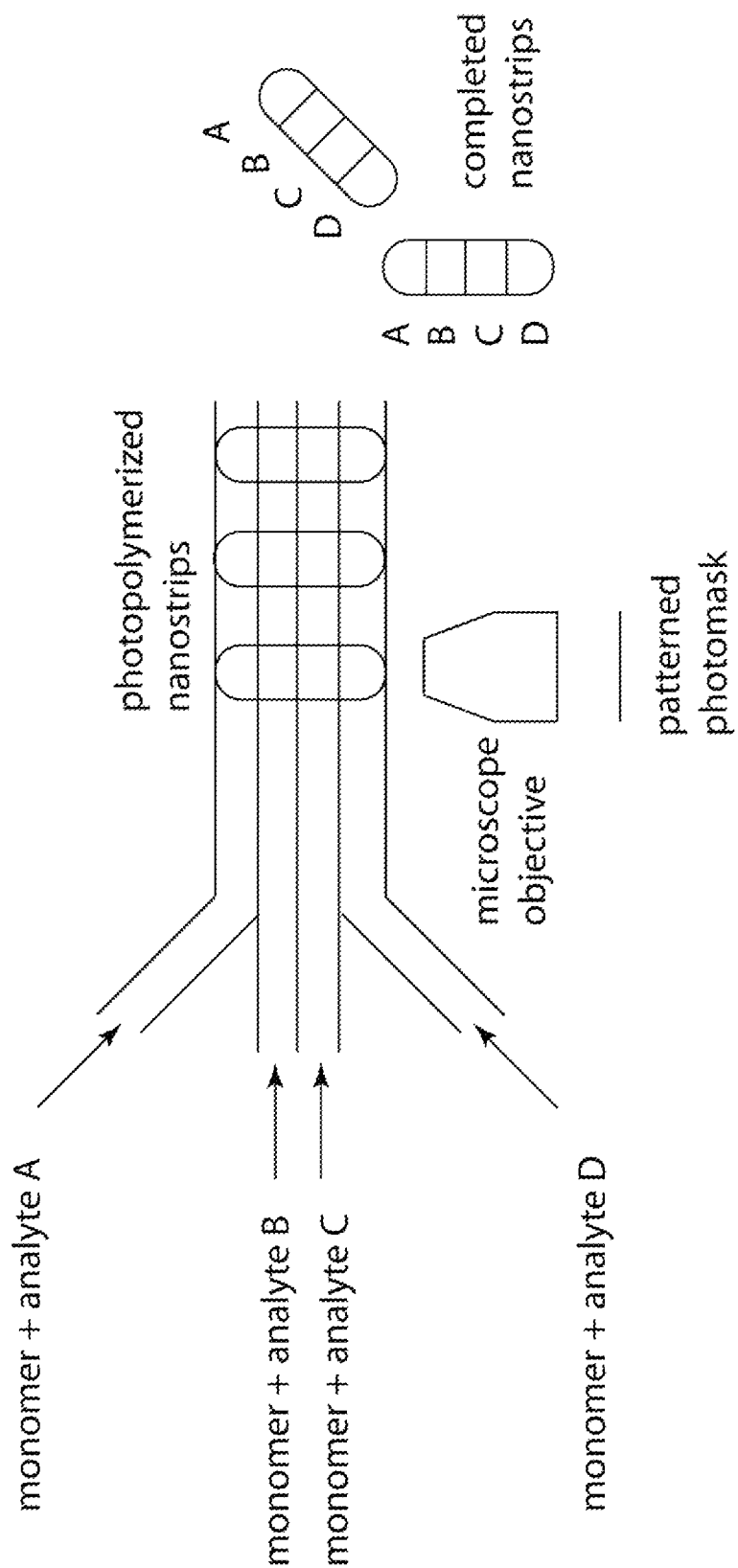
FIG. 2 is a magnified version of part of FIG. 1.

In a preferred embodiment, the system is cycled, so that three-way valve 22 is switched to divert the flow of gel-forming solution down waste arm 23. After the flow through passage 24 has stopped, the correct dose of polymerizing light is delivered to the monomers exposed at opening 30. After an appropriate length of time, the valve 22 is returned to the first position, resuming flow through the polymerizing zone. This creates an unpolymerized zone behind the polymerized region. After the polymerization zone has been filled with unpolymerized material, the valve 22 is again activated to initiate the next polymerization cycle FIG. 2 shows a perspective view of the polymerization process. In this embodiment, four streams enter the polymerization zone side-by-side, each stream containing polymerizable materials (exemplified by "monomer") and one analyte (sample or control). The streams are aligned to run in parallel through a photopolymerization zone. Light of a suitable frequency, or other polymerization-inducing means, is introduced through a lens, for example a microscope objective, and the beam of light is collimated by a photomask, here positioned below the lens, to form a bar-shaped emission. In this version, the polymers are continuously pushed into the photopolymerization zone, and the light is periodically blocked or turned off. The formed nanostrips are transported from the polymerization zone, ideally in the absence of light, and collected. A magnified sample is shown. In this example, there are four zones, a control zone plus gel segments that have binding sites selective for three types of molecule.

FIG. 2 also shows a cartoon of a completed nanostrip as used in the invention. The nanostrip contains three cells for assaying for various enzymes, and a control cell for calibration and for discrimination of ends.

Figure 3:
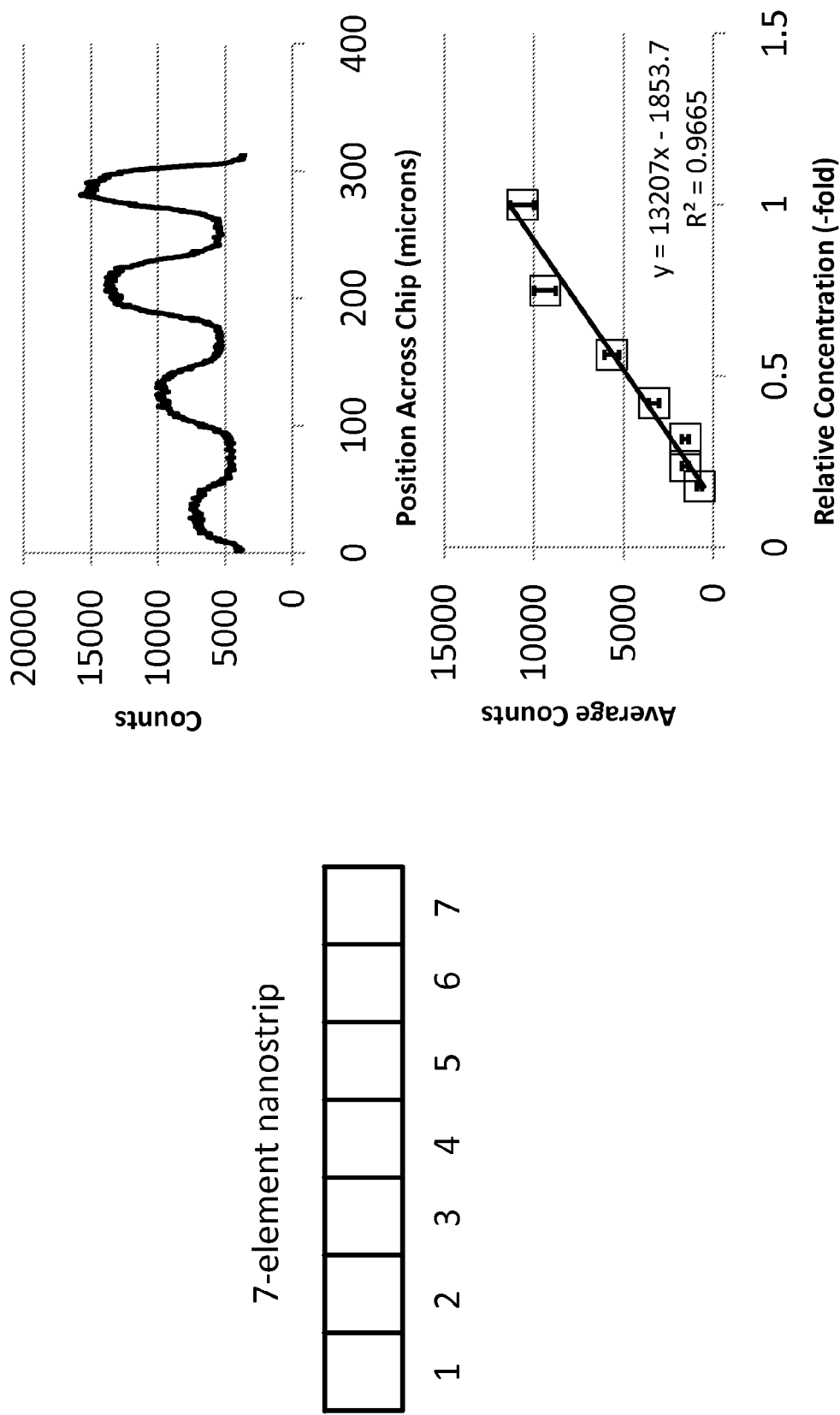
FIG. 3 shows a schematic of a nanostrip with seven zones, including four calibration zones and three empty zones, and the outputs and averaged outputs of calibration zones.

FIG. 3 shows a prototype seven-zone nanostrip produced by the process. Each of the zones contains either a control, or a certain amount of a fluorescing molecule. The observed counts are well-correlated with the standards' nominal concentrations.

Light sources, especially lasers, are preferred in the invention, as means both for fabrication of strips and for detection of analyte. Lasers used for analysis typically will have one discrete emission line. It is desirable to have the length of a zone, along the direction of travel of the strip during analysis, be significantly longer than the laser wavelength. With a laser wavelength of 0.5 to 1 micron (green to near IR), 1-2 microns is a minimum extent of a zone (twice the wavelength), and 5 to 50 microns is preferable in practice. Even greater nanostrip zone lengths may be required, depending on instrumentation response times, speed of flow, and other parameters. Note that a strip with 20 zones, each 100 microns wide, would be 2 millimeters in length.

Figure 4:
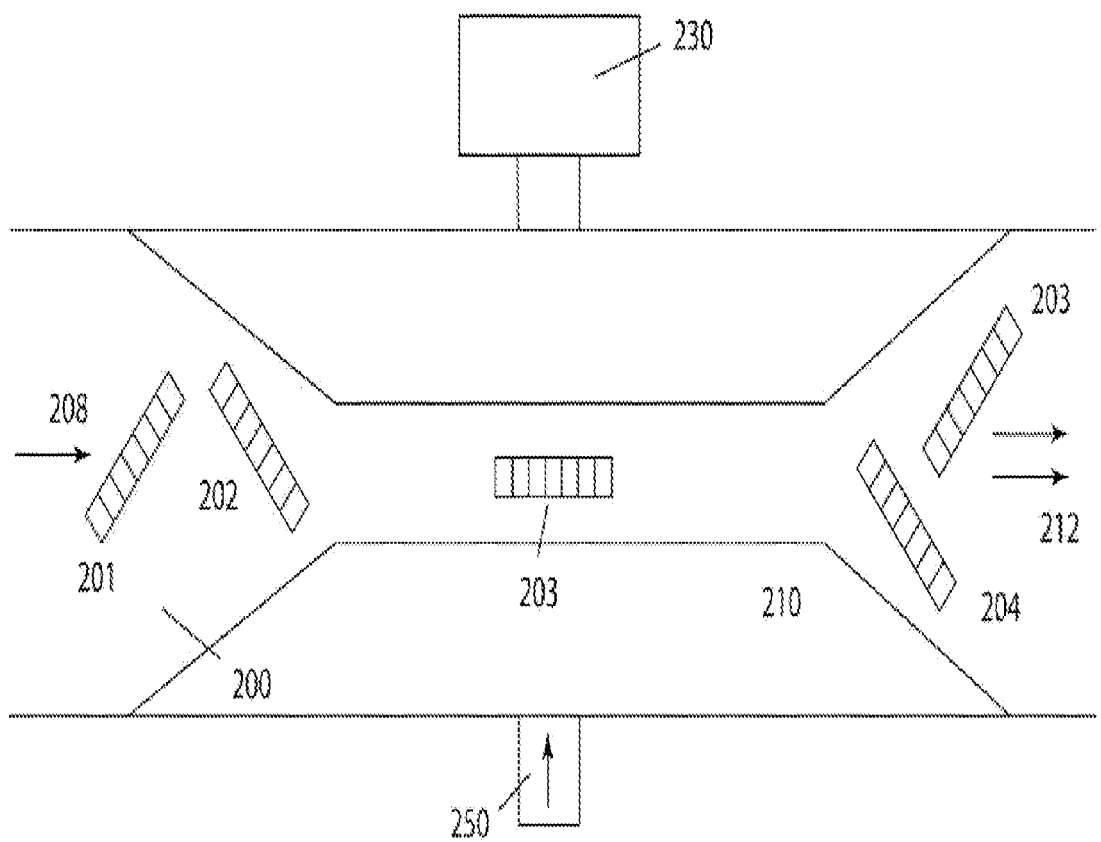
FIG. 4 shows an analysis section with a narrowing flow path to orient nanostrips while they are in the reading zone.

Since analysis will typically be conducted along the length of a nanostrip, it is preferable in one embodiment for the thickness and the width of the nanostrip to be the same, because light for analysis will pass through the width and/or the thickness of the nanostrip as the nanostrip passes longitudinally through the analytical beam during use. In the example of FIG. 2, the polymer solution is crosslinked to the depth of the channel (channel 24 in FIG. 1). In a preferred embodiment, the depth of the channel 24 is the same as the width of the polymerization zone 30. This results in a nanostrip with a roughly square cross-section. Since the nanostrip can "roll" when being flowed through a channel, it is desirable to have a nanostrip cross-section which will be relatively insensitive to the exact rotational position of the nanostrip when it is read during an assay. Positioning of standards next to sample zones will further minimize rotational effects. Averaging of responses from many nanostrips during an assay—for example, several hundred—will also smooth out the effects of a non-circular strip cross section. Orientation under shear can align strips having a variety of cross sections. FIG. 4 shows nanostrips entering a measuring zone. At the left, strips are flowing rightward through a channel which is significantly larger in diameter than the strips are long. The strips are not well oriented by the flow.

As the channel width smoothly drops to create a measurement zone, a velocity gradient is created. Since the leading end of the strip is "pulled" by the increased fluid velocity, which increases through the gradient zone, the nanostrip is quickly aligned with the flow, and then passes through an analysis beam ("laser line", in this example) in a well-oriented position that allows comparable exposures of the different sections to the analytical beam. It is also possible to manufacture nanostrip gels that are "flat", rather than square, in cross section, for example by reducing the width W of the strips during polymerization. Such strips are also useful in the invention. FIG. 2 shows a strip that is not square in cross-section. It is possible to orient flat nanostrips by narrowing the channel so that the strip will orient in a selected manner while penetrating the optical detection zone.

Once the strips have been formed, they are stored, optionally after a washing step, and later are used to perform a particular assay. Storage solutions will be controlled by the particular assays to be done—for example, preferring phosphate-buffered saline for some assays and tris-EDTA saline for others. Sterility of the strips is strongly preferred, and may be obtained by any appropriate means, such as sterile handling, treatment of strips with appropriate sterilizing chemicals, and/ or irradiation.

In use, the strips are mixed with fluids to be analyzed. If needed, the system may provide a wash step to remove any unbound molecules, either as a batch method, before entrance of the strips into the system, or in an in-line washing system, such as those described in our U.S. application Ser. Nos. 13/374,157; 13/374,683; and 61/630,591. Optionally, other appropriate reagents and materials may be added to the assay system, during storage or at the time of use.

Reaction between the sample and the nanostrips is fast, because the nanostrips are preferably small—typically 15-20 microns wide, and having a thickness ranging from several microns up to the width of the strip.

In one embodiment, the nanostrips are dried in a film on the inside of a small diameter tube. Then the tube is placed in the flow, and sample to be analyzed is flowed through the tube, hydrating and entraining the nanostrips in the tube. Equilibration and/or reactions between the sample and the nanostrips is fast, because the nanostrips are small.

Use of the Nanostrips

In an assay using the system of the invention, a solution containing a number of strips carrying appropriate binding sites is mixed with a sample for assay—for example, a sample of serum from a patient—and optionally with additional reagents, such as fluorescent antibodies or other binding reagents. The sample may contain biomarkers, hormones, proteins, nucleic acids, and/ or other clinically relevant samples that need to be measured. In a preferred embodiment, a binding molecule immobilized on the nanostrip binds to the clinically relevant molecule to be measured (the analyte), directly or indirectly. In many assays, a detection molecule, such as an antibody, a nucleic acid, or another molecule that can bind to the analyte, will usually carry an indicator such as a chromophore, or a fluorescent group. The detection molecule is mixed with the sample and the nanostrips, and binds to the analyte so as to make it detectable. The detection molecule can be measured by any convenient means, including optical absorbance or emission (fluorescence), at one or more wavelengths. Binding in the system may occur in a classical mode, in which a mixture is prepared containing the sample to be analyzed, nanostrips carrying binding sites for the analyte of interest, and indicator molecules. The sample is then incubated to allow the interactions to occur, and fluorescence or other signal is then observed by flowing the mixture through the detection region of a meter. Surprisingly, it has been found that prolonged static mixing of the sample and the nanostrips is not necessary for these analyses. It is believed that because the scale of the critical region, i.e., the thickness of the nanostrip, is so small, the required time to equilibrate molecules to be detected into the gel of the nanostrip is very short. It has been found in practice that it is possible for numerous assays to be evaluated simply by mixing the ingredients—for example by flowing a solution containing analytes through a capillary coated with dried nanostrips—and flowing the mixture directly to a detection region.

The mixed sample is analyzed by flowing it through a detection cell for analysis. The analysis system is illustrated schematically in FIG. 4. Five strips 201-205 are depicted in a flow stream 200 entering the analysis cell at 208 and proceeding through an analysis zone 210 to an exit zone 212.

As noted above, the shear forces that occur as the flow enters the analysis zone orient the nanostrips into approximately straight forms as they pass into the analysis zone. Moreover, at sufficient dilution, samples will be well separated, and will almost entirely have a minimum separation distance, such as two nearby samples 201, 202 in FIG. 4. Samples that touch or overlap will be read as having abnormal lengths of time in the system, or will have abnormal optical depth, or will cause excessive pressure drops. Such signals can be analyzed, and used to exclude the data from that particular strip.

Analysis can be performed by any technique with the desired sensitivity and response time. One suitable analytical method involves the stimulation of chromophores in the system with laser light, and observing the fluorescence emission from molecules bound in the nanostrip being assayed.

The nanostrips and their zones lead to desired optical changes because detection analytes are co-polymerized into their matrix. Binding of clinically relevant molecules to these detection analytes leads to detectable changes in the nanostrips. Often, a detection reagent is further added to the mixture to facilitate fluorescence. For instance, a fluorescently labeled antibody or nucleic acid can be utilized to bind to the immobilized clinical analyte to make it fluorescent.

It is important to choose an effective velocity of a nanostrip past the optical sensor 230 (see FIG. 4) such that each of the segments of each nanostrip can be sampled during the transit of the optical beam 250. At least one sampling in each zone during chip passage is preferred. Having multiple samples is more preferred, and sampling at least three times during transit is strongly preferred. Sampling each segment five to ten times is desirable if other system requirements can be met. Use of a second detection system downstream of a first detection system is another way to increase the number of samples, but is less desirable. FIG. 3 shows the detection results of a flowing nanostrip having four zones containing a bound fluorescent standard, and it is clear that the four levels of a standard can be distinguished and give quantitatively useable results.

Assay Identification by Bar Code

The pattern of zones, read along the length of the strip, can be made to constitute an implicit "barcode" identifying the assay performed. It has been proposed (e.g. White & Gilmanshin, U.S. Pat. No. 7,595,160) to use an analysis system having an explicit barcode property—i.e., having several zones on a strip serving only as a barcode system to identify the assay, essentially a micro version of a conventional bar code. However, that option is markedly less efficient in its use of the limited number of zones that are practically available. Moreover, as presented, it can require several parallel lanes on a strip to make enough digits to identify an analysis type.

While there is no sharp cutoff, there are practical difficulties both in making strips with large numbers of zones, and in ensuring that such strips are sufficient rigid to pass the analytical cell of the system with reasonably straight orientation along the flow path. In work to date, a nanostrip with fewer than about 20 zones is preferred, and more preferably twelve or fewer zones are used. Because the number of zones is limited, the set of zones is a limited resource, and must be used efficiently to provide robust, redundant identification of the nature of the test and the orientation of the strip.

An efficient use of the limited number of zones on a strip is to combine the mutual spacing of zones containing controls with zones containing samples to be measured, and to further use said sample and control zones as partial or complete portions of bar-code type identification of the nature of the assay. Any of these can also be used to encode the "endedness" of nanostrips.

Consider FIG. 5A. This is a simple strip with nine zones. Five zones (C1-C5) are controls for various levels of the analyte—for example, an antibody in the serum against a viral antigen. Four sample zones (S1-S4) are provided containing fixed levels of the antigen. The antigen is bound into the nanostrip gel during fabrication, or can be loaded into an activated nanostrip after fabrication and controlled storage.

The top line in FIG. 5, i.e., FIG. 5A, shows five control zones, C1-C5, proceeding monotonically—for example, 100%, 75%, 50%, 25%, 0% of a value; and four sample zones, S1-S4, nominally identical (same sample). It would be straightforward to find the level of the analyte in the clinical sample—especially since the assay system will interrogate several hundred nanostrips in the course of a short assay. And identification of which end of the sample is which would be straightforward. But the system has no way to identify what was assayed—the type of analysis would have to be entered by the operator. It is preferred, especially for a system destined for remote areas, that operator skill not be required to produce a value of a clinical analyte, or to record it. Means for identifying an assay, as well as producing results of an assay, are an important part of a clinical analysis system.

Two methods have been devised for adding bar code functionality to such a system. A first method is to use a different wavelength of light (or other measuring function) to read the same strip. FIG. 5B shows a barcode of the invention, having a "barcode lane" (X) or no lane (blank). The code for this assay is "X_XX_X_" (or equivalently, 101100100). The physical embodiment of the barcode could be the deposition (or lack thereof) of a material having a fluorescent emission wavelength that is excited and/or read at a different wavelength from the wavelength at which the samples and controls are excited and read. For example, the sample and calibration zones could be excited at 532 nm and read at 575 nm, and the barcode function could be excited at 633 nm, and read at 690 nm. Using such procedures, the assay of strip B could easily be distinguished with another assay using similar wavelengths of emission and reading, as illustrated in line C, where both the pattern and the order of controls is different from that in line B.

In this particular example, the reading of the controls for the test provides end orientation. Moreover, the arrangement of the control zones can provide additional binary digits of information concerning the assay, as long as means for finding the orientation of the nanostrip are provided. There are numerous ways to accomplish the orientation function, in addition to bar-coding of controls. For example, a zone could be opaque, or reflective, or electrically conducting.

Moreover, the calibration zones could be in duplicate (or triplicate or more), and not necessarily in order, thereby providing redundancy both for the calibration curve and also for the barcode. In this embodiment, it is possible for the pattern of calibration zones to form a barcode, and thereby allow the assay to be read and identified with a single excitation laser and a single detector.

In the above discussion, an assay which determines the level of only one analyte is considered. However, it is possible to measure more than one analyte with a single nanostrip. For example, a strip could have three measurement zones and four calibration zones for each of a first and a second assay. This provides up to fourteen zones for use in the barcode of the assay. The instrument could use such information to select the particular assay out of 8000 others, and could also identify the orientation of the nanostrip in the reader.

It should be recalled, when contemplating nanostrips with large numbers of zones, that in the present invention, all of the complexity of a sample reading is built into the nanostrip. Each of the N zones derives from a particular polymerizable solution that was provided at the time of manufacture. The bar coding function allows the reading of values of one or more samples and one or more calibration sets for the reading, as well as a definitive assay identification, with the "organizational" work being performed by computing means in the instrument. The definitive assay identification can be encoded in one or both of a particular pattern of control lanes and a pattern of purely location lanes (X).

Additional sources of calibration can be added to an assay to further establish the relative levels of absorbance, emission or related properties of the stock nanostrips of the particular assay. For example, and without limitation, one or both of the length of a nanostrip and the width of a nanostrip may be identified during its passage through a sensor, and at least one of said length and width could be used to contribute an input to a bar code for said nanostrip. Such a nanostrip might have a single zone and be differentiated by its length or width, with the single-zone property serving to indicate that the particular strip is a standardizing strip and not a data providing strip. Moreover, such a single zone nanostrip can have a known ratio of signals at different wavelengths and can serve as a standard reference for intensity in the system. In all of these systems, one or more nanostrips, that are identifiable as standardizing nanostrips by at least one of number of zones and ratios of signals at different wavelengths, can be used for calibrating signal intensity of the instrument.

Moreover, because all of these processes are digital and each nanostrip is individually assayed, it is possible to combine more than one type of nanostrip in a given assay. The barcode of each type of nanostrip tells the system how to interpret the particular readings from a passing nanostrip.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference, where such incorporation is permitted. Nothing herein is to be construed as an admission that the invention is not entitled to antedate such disclosure by virtue of prior invention, where relevant. Those skilled in the art will recognize, or be able to ascertain using no more than routine experimentation, many equivalents to the specific embodiments of the invention described herein. Such equivalents are intended to be encompassed by the following claims.

The invention claimed is:

1. An analytical nanostrip for use in a flow analysis system for performing an assay on a sample in which the nanostrip has been mixed, the nanostrip comprising:
    an elongate strip having a plurality of assay zones thereon configured in an orientation,
    a first of said plurality of assay zones being both a first measurement zone and a first zone for identifying the assay, and
    a second of the plurality of assay zones being both a control zone and a second zone for identifying the assay and comprising a first fluorescent material having a first fluorescent emission wavelength for conveying calibration information and a second fluorescent material having a second fluorescent emission wavelength for conveying information identifying the assay.

2. The analytical nanostrip of claim 1, wherein the first assay zone functions as the first measurement zone when measured with light of a first wavelength and the first identification zone when measured with light of a second wavelength.

3. The analytical nanostrip of claim 1 wherein at least two other assay zones are control zones having varying values of analyte and configured in an orientation.

4. The analytical nanostrip of claim 3 wherein the orientation of the control zones is used to encode the orientation of the assay zones.

5. The analytical nanostrip of claim 3 wherein the orientation of the control zones is used to encode the type of the assay.

6. The analytical nanostrip of claim 1 wherein the nanostrip has a square cross-section.

7. The analytical nanostrip of claim 3 wherein the plurality of the control zones have different optical properties, and the different optical properties are used to provide a calibration curve.

8. The analytical nanostrip of claim 1 wherein at least one of the length or the width of the nanostrip is used to identify the assay.

9. The analytical nanostrip of claim 1 wherein the nanostrip is a standardizing nanostrip to be used for calibrating the signal intensity of a reader for the nanostrip.

10. The analytical nanostrip of claim 1 wherein the first assay zone functions as the first measurement zone when measured with light of a first wavelength and the width of the first assay zone serves the function of an identification zone.

11. The analytical nanostrip of claim 1 wherein two other assay zones perform different assays.

12. The analytical nanostrip of claim 1, two or more of the plurality of assay zones being both a measurement zone and a zone identifying the assay, the two or more assay zones providing a bar code of binary values readable by a light having a first wavelength.

13. The analytical nanostrip of claim 1 wherein the orientation of the control zone relative to the first measurement zone identifies the assay.

14. A method of clinical analysis using the nanostrip of claim 1, the method comprising:
    mixing the nanostrip with the sample to be analyzed to enable the sample to interact with each of the plurality of assay zones;
    flowing the mixture of the sample and the nanostrip in a stream to a detection area;
    determining a standardizing signature of the sample correlating at least one property of any of the plurality of assay zones to a discrete position of the nanostrip; and
    determining a measuring signature of the sample by measuring at least one sample property in at least one of the plurality of assay zones on the nanostrip.

15. The method of claim 14 further comprising determining a directionality of the nanostrip using one other of the plurality of assay zones providing an orientation function.

16. A portable system for the analysis of clinical samples, the system comprising:
    the nanostrips of claim 1;
    a channel having a width less than the length of the nanostrips for orienting and flowing the nanostrips past at least one analysis beam; and
    the at least one analysis beam for interrogating the nanostrips.

17. Nanostrip of claim 1 wherein at least one of the plurality of assay zones is an orientation zone, the orientation zone being selected from the group of an opaque zone, a reflective zone, and an electrically conductive zone.

* * * * *